United States Patent
Simandan et al.

(10) Patent No.: US 7,528,273 B2
(45) Date of Patent: May 5, 2009

(54) AQUEOUS CATALYTIC PROCESS FOR THE PREPARATION OF THIOCARBOXYLATE SILANE

(75) Inventors: Tiberiu Ladislau Simandan, Marietta, OH (US); Thomas Link Guggenheim, Mt. Vernon, IN (US)

(73) Assignee: Momentive Performance Materials Inc., Albany, NY (US)

( * ) Notice: Subject to any disclaimer, the term of this patent is extended or adjusted under 35 U.S.C. 154(b) by 564 days.

(21) Appl. No.: 11/105,916

(22) Filed: Apr. 14, 2005

(65) Prior Publication Data

US 2006/0235236 A1 Oct. 19, 2006

(51) Int. Cl.
C07F 7/08 (2006.01)
(52) U.S. Cl. ..................................... 556/429
(58) Field of Classification Search .................. 556/429
See application file for complete search history.

(56) References Cited

U.S. PATENT DOCUMENTS

| | | | |
|---|---|---|---|
| 5,081,298 A | 1/1992 | Brunelle | 564/236 |
| 5,116,975 A | 5/1992 | Brunelle | 554/86 |
| 5,132,423 A | 7/1992 | Brunelle et al. | 544/162 |
| 5,229,482 A | 7/1993 | Brunelle | 528/125 |
| 5,830,974 A | 11/1998 | Schmidhauser et al. | 528/125 |
| 5,905,150 A | 5/1999 | Simonian et al. | 544/221 |
| 5,907,025 A | 5/1999 | Brunelle | |
| 5,908,915 A | 6/1999 | Brunelle | 528/170 |
| 6,028,203 A | 2/2000 | Brunelle et al. | 548/154 |
| 6,235,934 B1 | 5/2001 | Caringi et al. | 564/241 |
| 6,570,038 B1 | 5/2003 | Caringi et al. | 564/241 |
| 6,706,897 B1 | 3/2004 | Brunelle et al. | 549/241 |
| 6,777,569 B1 | 8/2004 | Westmeyer et al. | 556/429 |

FOREIGN PATENT DOCUMENTS

| | | |
|---|---|---|
| EP | 0900801 | 3/1999 |
| WO | WO2005/007660 | 1/2005 |
| WO | WO2005/007661 | 1/2005 |
| WO | WO2005007661 | 1/2005 |

Primary Examiner—Peter G O'Sullivan
(74) Attorney, Agent, or Firm—Dominick G. Vicari

(57) ABSTRACT

An aqueous process is described in which thiocarboxylate silane is produced from haloalkyl silane by reaction of the haloalkyl silane with an aqueous solution of thiocarboxylate salt in the presence of a catalytically effective amount of alkylguanidinium salt.

14 Claims, No Drawings

AQUEOUS CATALYTIC PROCESS FOR THE PREPARATION OF THIOCARBOXYLATE SILANE

BACKGROUND OF THE INVENTION

Thiocarboxylate silanes are extensively used in rubber applications, especially for tires. WO 2005/007660 describes a process in which thiocarboxylate silane is prepared from a corresponding alkanoyl chloride and a chloroalkyltrialkoxy silane using trialkylamines to scavenge the hydrochloric acid by-product. The process requires the use of a stoichiometric amount of amine that is recycled after treatment with caustic to the corresponding hydrochloride. The process is relatively complex and uneconomical.

WO 2005/007661 describes a process for the preparation of thiocarboxylate silane in an aqueous process in the presence of a phase transfer catalyst such as a quaternary ammonium salt or a phosphonium salt. The rate of reaction in this process is low requiring large amounts of catalyst and, as a result, complicated purification procedures.

The manufacture of blocked mercaptosilane from an acyl halide is known from U.S. Pat. No. 6,777,569, but results in a less pure product and a lower yield.

SUMMARY OF THE INVENTION

In accordance with the present invention, there is provided a process for the preparation of thiocarboxylate silane which comprises reacting an aqueous solution of salt of thiocarboxylic acid with a haloalkyl silane in the presence of a catalytically effective amount of alkylguanidinium salt phase transfer catalyst to provide thiocarboxylate silane.

The drawbacks in the known processes of preparing thiocarboxylate silane referred to above are addressed and overcome by the process described herein. The use of alkylguanidinium salt as catalyst permits the use of higher reaction temperatures due to the much higher thermal stability of compounds of this type. With the use of higher reaction temperatures, the overall kinetics of the reaction is dramatically improved. The amount of catalyst usage and the time cycle can be cut considerably, e.g., by more than 50%, while the yield and quality of the product are significantly improved. The rag layer usually present between the aqueous and the organic phases due to the high level of catalyst usage in the previous systems is completely absent herein allowing for easy purification and processing of the waste water.

The foregoing process for the preparation of thiocarboxylate silane (e.g. an NXT™ silane such as 3-octanoylthio-1-propyltriethoxysilane) employs an aqueous thiocarboxylate salt reactant which can be prepared from readily available carboxylic acid derivatives, in particular, acid chlorides.

DETAILED DESCRIPTION OF THE INVENTION

Silane Structures

In accordance with the present invention as hereinafter more fully described and claimed, there is provided a process for the preparation of thiocarboxylate silane which comprises reacting an aqueous solution of thiocarboxylic acid salt with a haloalkyl silane in the presence or absence of a catalytically effective amount of alkylguanidinium salt to provide thiocarboxylate silane.

The invention herein provides a simple and efficient process of the manufacture of thiocarboxylate silane. The process requires no solvent other than water, uses existing aqueous sulfide raw materials as the sulfur source and requires no hazardous alkali metals or hydrogen sulfide as feedstock.

The thiocarboxylate silanes, whose preparation by an aqueous route is described herein, may be represented by Formulae 1, 2, and 3:

$$(R—Y—S—)_a G^2(—SiX_3)_c \quad (1)$$

$$G^1[—Y—S-G^2(—SiX_3)_c]_a \quad (2)$$

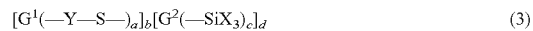

$$[G^1(—Y—S—)_a]_b[G^2(—SiX_3)_c]_d \quad (3)$$

wherein Y is carbonyl, C(=O); each occurrence of R is chosen independently from the set of groups comprising hydrogen, alkyl groups that may or may not contain unsaturation, alkenyl groups, alkynyl groups, aryl groups and aralkyl groups, with each R containing from 0 to 30 carbon atoms; each separate occurrence of $G^1$ and $G^2$ is independently R or a polyvalent group derived by substitution of an alkyl, alkenyl, aryl or aralkyl group, wherein $G^1$ and $G^2$ can contain from 1 to 40 carbon atoms, with the proviso that $G^1$ and $G^2$ are not hydrogen; each separate occurrence of $G^1$ is independently R or a polyvalent group derived by substitution of an alkyl, alkenyl, aryl or aralkyl group, wherein $G^1$ can contain from 1 to 40 carbon atoms; each separate occurrence of $G^2$ is independently a polyvalent (divalent or higher-valent) group derived by substitution of an alkyl, alkenyl, aryl or aralkyl group, wherein $G^1$ and $G^2$ can contain from 1 to 40 carbon atoms; each occurrence of X is independently a member selected from the group consisting of RO—, $R_2C=NO—$, $R_2NO—$ or $R_2N—$, —R, and $—(OSiR_2)_t (OSiR_3)$, wherein each R is as above and at least one X is not —R; each occurrence of the subscript a is independently an integer from 1 to 6; each occurrence of the subscript b is independently an integer from 1 to 100; each occurrence of the subscript c is independently an integer from 1 to 6; and, each occurrence of the subscript d is independently an integer from 1 to 100.

As used herein, alkyl includes straight, branched and cyclic alkyl groups; alkenyl includes any straight, branched, or cyclic alkenyl group containing one or more carbon-carbon double bonds, where the point of substitution can be either at a carbon-carbon double bond or elsewhere in the group; and alkynyl includes any straight, branched, or cyclic alkynyl group containing one or more carbon-carbon triple bonds and optionally also one or more carbon-carbon double bonds as well, where the point of substitution can be either at a carbon-carbon triple bond, a carbon-carbon double bond, or elsewhere in the group. Specific examples of alkyls include methyl, ethyl, propyl and isobutyl. Specific examples of alkenyls include vinyl, propenyl, allyl, methallyl, ethylidenyl norbornane, ethylidene norbornyl, ethylidenyl norbornene and ethylidene norbornenyl. Specific examples of alkynyls include acetylenyl, propargyl and methylacetylenyl.

As used herein, aryl includes any aromatic hydrocarbon from which one hydrogen atom has been removed; aralkyl includes any of the aforementioned alkyl groups in which one or more hydrogen atoms have been substituted by the same number of like and/or different aryl (as defined herein) substituents; and arenyl includes any of the aforementioned aryl groups in which one or more hydrogen atoms have been substituted by the same number of like and/or different alkyl (as defined herein) substituents. Specific examples of aryls include phenyl and naphthalenyl. Specific examples of aralkyls include benzyl and phenethyl. Specific examples of arenyls include tolyl and xylyl.

As used herein, cyclic alkyl, cyclic alkenyl, and cyclic alkynyl also include bicyclic, tricyclic, and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, ethylcyclohexyl, ethylcyclohexenyl, cyclohexylcyclohexyl and cyclododecatrienyl.

The key functional group (—YS—) present in the silanes of the present invention is the thiocarboxylate ester group, —C(=O)S— (any silane with this functional group is a "thiocarboxylate ester silane"). The silanes of the present invention include those wherein Y is $R^0C(=O)$— representing a simple subset of the structures represented by Formulae 1-2.

Examples of structures within the set wherein Y is equal to $R^0C(=O)$— include those wherein $R^0$ has a primary carbon attached to the carbonyl and is advantageously a $C_2$-$C_{20}$ straight- or branched-chain alkyl, more particularly a $C_6$-$C_{18}$ straight-chain alkyl. Especially advantageous herein are $C_6$-$C_{14}$ straight-chain alkyls.

Representative examples of G include monovalent hydrocarbon groups such as those described above for R; phenylene; —$(CH_2)_n$— wherein n is 1 to 20, which represent the terminal straight-chain alkyls further substituted terminally at the other end such as —$CH_2$—, —$CH_2CH_2$—, —$CH_2CH_2CH_2$—, and —$CH_2CH_2CH_2CH_2CH_2CH_2CH_2CH_2$— and their beta-substituted analogs such as —$CH_2(CH_2)_mCH(CH_3)$— where m is zero to 17; —$CH_2CH_2C(CH_3)_2CH_2$—; the structure derivable from methallyl chloride, —$CH_2CH(CH_3)CH_2$—; any of the structures derivable from divinylbenzene such as —$CH_2CH_2(C_6H_4)CH_2CH_2$— and —$CH_2CH_2(C_6H_4)CH(CH_3)$— where the notation $C_6H_4$ denotes a disubstituted benzene ring; any of the structures derivable from dipropenylbenzene such as —$CH_2CH(CH_3)(C_6H_4)CH(CH_3)CH_2$— where the notation $C_6H_4$ denotes a disubstituted benzene ring; any of the structures derivable from butadiene such as —$CH_2CH_2CH_2CH_2$—, —$CH_2CH_2CH(CH_3)$— and —$CH_2CH(CH_2CH_3)$—; any of the structures derivable from piperylene such as —$CH_2CH_2CH_2CH(CH_3)$—, —$CH_2CH_2CH(CH_2CH_3)$— and —$CH_2CH(CH_2CH_2CH_3)$—; any of the structures derivable from isoprene such as —$CH_2CH(CH_3)CH_2CH_2$—, —$CH_2CH(CH_3)CH(CH_3)$—, —$CH_2C(CH_3)(CH_2CH_3)$—, —$CH_2CH_2CH(CH_3)CH_2$—, —$CH_2CH_2C(CH_3)_2$— and —$CH_2CH[CH(CH_3)_2]$—; any of the isomers of —$CH_2CH_2$-norbornyl-, —$CH_2CH_2$-cyclohexyl-; any of the diradicals obtainable from norbornane, cyclohexane, cyclopentane, tetrahydrodicyclopentadiene or cyclododecene by loss of two hydrogen atoms; the structures derivable from limonene, —$CH_2CH(4$-methyl--$C_6H_9$—$)CH_3$, where the notation $C_6H_9$ denotes isomers of the trisubstituted cyclohexane ring lacking substitution in the 2 position; any of the monovinyl-containing structures derivable from trivinylcyclohexane such as —$CH_2CH_2(vinylC_6H_9)CH_2CH_2$— and —$CH_2CH_2(vinylC_6H_9)CH(CH_3)$— where the notation $C_6H_9$ denotes any isomer of the trisubstituted cyclohexane ring; any of the monounsaturated structures derivable from myrcene containing a trisubstituted C=C such as —$CH_2CH[CH_2CH_2CH=C(CH_3)_2] CH_2CH_2$—, —$CH_2CH[CH_2CH_2CH=C(CH_3)_2]CH(CH_3)$—, —$CH_2C[CH_2CH_2CH=C(CH_3)_2] (CH_2CH_3)$—, —$CH_2CH_2CH[CH_2CH_2CH=C(CH_3)_2]CH_2$—, —$CH_2CH_2(C—)(CH_3) [CH_2CH_2CH=C(CH_3)_2]$ and —$CH_2CH[CH(CH_3)][CH_2CH_2CH=C(CH_3)_2]]$—; and, any of the monounsaturated structures derivable from myrcene lacking a trisubstituted C=C such as —$CH_2CH(CH=CH_2)CH_2CH_2CH_2C(CH_3)_2$—, —$CH_2CH(CH=CH_2)CH_2CH_2CH[CH(CH_3)_2]$—, —$CH_2C(=CH—CH_3)CH_2CH_2CH_2C(CH_3)_2$—, —$CH_2C(=CH—CH_3)CH_2CH_2CH[CH(CH_3)_2]$—, —$CH_2CH_2C(=CH_2)CH_2CH_2CH_2C(CH_3)_2$—, —$CH_2CH_2C(=CH_2)CH_2CH_2CH[CH(CH_3)_2]$—, —$CH_2CH=C(CH_3)_2CH_2CH_2CH_2$ $C(CH_3)_2$— and —$CH_2CH=C(CH_3)_2CH_2CH[CH(CH_3)_2]$. Some specific structures for $G^1$, $G^2$ and $G^3$ are —$CH_2$—, —$CH_2CH_2$—, —$CH_2CH_2CH_2$—, —$CH_2CH(CH_3)CH_2$— and any of the diradicals obtained by 2,4 or 2,5 disubstitution of the norbornane-derived structures listed above. The structure —$CH_2CH_2CH_2$— is particularly advantageous.

Representative examples of R groups are branched and straight-chain alkyls of 1 to 30 carbon atoms or more such as methyl, ethyl, propyl, isopropyl and butyl; phenyl; benzyl; tolyl; and, allyl. Some specific R groups are $C_1$ to $C_4$ alkyls and H.

Representative examples of X are methoxy, ethoxy, isobutoxy, propoxy, isopropoxy and oximato. Methoxy and ethoxy are particularly advantageous.

Included among the embodiments herein are those in which p is 0 to 2; X is RO—; R is hydrogen, methyl, ethyl, propyl, butyl or isopropyl; and, G is a substituted phenyl or substituted $C_2$ to $C_{20}$ straight-chain alkyl. Other specific embodiments include structures of the form $X_3SiGSC(=O)GC(=O)SGSiX_3$ wherein G is a divalent hydrocarbon.

Specific embodiments include those wherein p is zero, X is ethoxy and G is a $C_6$-$C_{14}$ straight-chain alkyl.

Representative examples of the silanes whose preparation is described in the present invention include 2-triethoxysilyl-1-ethyl thioacetate; 2-trimethoxy-silyl-1-ethyl thioacetate; 2-(methyldimethoxysilyl)-1-ethyl thioacetate; 3-trimethoxysilyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxy-silyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 1-(1-oxo-2-thia-5-triethoxysilylpenyl)benzoic acid; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxy-silyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctanoate, also known as 3-trimethoxysilyl-1-propyl thioloctoate and 3-trimethoxysilyl-1-propyl thiocaprylate; 3-triethoxysilyl-1-propyl thiopalmitate; 3-triethoxysilyl-1-propyl thiooctanoate, also known as 3-triethoxysilyl-1-propyl thioloctoate and 3-triethoxysilyl-1-propyl thiocaprylate; 3-triethoxysilyl-1-propyl thiodecanoate; 3-triethoxysilyl-1-propyl thiododecanoate, also known as 3-triethoxysilyl-1-propyl thiolaurate; 3-triethoxysilyl-1-propyl thiotetradecanoate, also known as 3-triethoxysilyl-1-propyl thiomyristate; 3-triethoxysilyl-1-propyl thiobenzoate; 3-triethoxysilyl-1-propyl thio-2-ethylhexanoate; 3-triethoxysilyl-1-propyl thio-2-methylheptanoate; bis-(3-triethoxysilyl-1-propyl)dithiophthalate; bis-(3-triethoxysilyl-1-propyl) dithio-iso-phthalate; bis-(3-triethoxysilyl-1-propyl)dithio-tere-phthalate; bis-(3-triethoxysilyl-1-propyl) dithiosuccinate; bis-(3-triethoxysilyl-1-propyl) dithiooxalate; bis-(3-triethoxysilyl-1-propyl)dithiosebacate; and, bis-(3-triethoxysilyl-1-propyl)dithioadipate.

The thiocarboxylate silane compositions included herein may be prepared as various mixtures of individual thiocarboxylate silane components, optionally including other species as well, including wherein synthetic methods result in a distribution of various silanes and including wherein mixtures of the starting components are employed for the purpose of generating mixtures of thiocarboxylate silane products. Moreover, it is understood that the partial hydrolyzates and/or condensates of these thiocarboxylate silanes (i.e., thiocarboxylate siloxanes and/or silanols) may also be encompassed by the thiocarboxylate silanes herein, in that these partial hydrolyzates and/or condensates will be a side product of most methods of manufacture of the thiocarboxylate silanes or can occur upon storage of the thiocarboxylate silanes, especially in humid conditions, or under conditions in which residual water remaining from their preparation is not completely removed subsequent to their preparation.

Preparation of Thiocarboxylate Silane

The process herein for the preparation of thiocarboxylate-functional silane involves the reaction between aqueous thiocarboxylic acid salt (i.e., an aqueous solution containing thiocarboxylate anion) with a haloalkyl silane in the presence of a catalytically effective amount of alkylguanidinium salt. Optionally, mixtures of aqueous thiocarboxylate salts and/or haloalkyl silanes can be used in which case mixtures of thiocarboxylate silanes will be obtained.

As used herein, the expression "haloalkyl silane" refers to any silane whose structure can be represented by Formula 3. Thus, "haloalkyl silane" includes silanes with one or more halogen substitutions for hydrogen on their hydrocarbon groups, as well as other substitutions which would represent potential leaving groups during nucleophilic substitution reactions, as described below. A general structure for the thiocarboxylate salt reactant is given in Formula 4 as follows:

A general structure for the haloalkyl silane reactant is given in Formula 5 as follows:

In formulae 4 and 5, each occurrence of $G^1$ and $G^2$ is independently R or a polyvalent group derived by substitution of an alkyl, alkenyl, aryl or aralkyl group, wherein $G^1$ and $G^2$ can contain from 1 to 40 carbon atoms, with the proviso that $G^1$ and $G^2$ are not hydrogen, and where $G^1$ and/or $G^2$ is R, each occurrence of R is chosen independently from the set of groups comprising hydrogen, alkyl groups that may or may not contain unsaturation, alkenyl groups, alkynyl groups, aryl groups, and aralkyl groups, with each R containing from 0 to 30 carbon atoms; Y is carbonyl, C(=O); each occurrence of M is an alkali metal; ammonium; or a mono-, di-, or tri-substituted ammonium; each occurrence of L is a halogen atom (i.e., F, Cl, Br, or I), sulfonate group, sulfinate group, or carboxylate group; each occurrence of X is independently a member selected from the group consisting of RO—, $R_2C$=NO—, $R_2NO$— or $R_2N$—, —R, and —($OSiR_2$)$_t$ ($OSiR_3$), wherein each R is as previously defined and at least one X is not —R; each occurrence of the subscript a is independently an integer from 1 to 6; each occurrence of the subscript b is independently an integer from 1 to 100; each occurrence of the subscript c is independently an integer from 1 to 6; each occurrence of the subscript d is independently an integer from 1 to 100; and, each occurrence of the subscript f is independently an integer from 1 to 6, with the proviso that ab=df.

M is an alkali metal; ammonium; or a mono-, di- or tri-substituted ammonium. Thus, M is typically a monocation, meaning it occurs as a cation, typically with a single positive charge. Dicationic ions could also be used in cases where their thiocarboxylate salts are available and are sufficiently soluble in water. As such, M is the counterion to the anionic thiocarboxylate, $[(ROC(=O)—)_p(G)_j]$-Y—S$^-$. Representative examples of M are sodium, potassium, ammonium, methyl ammonium and triethyl ammonium. Sodium, potassium and ammonium are especially advantageous.

L is a halogen atom (i.e., F, Cl, Br, or I), sulfonate group, sulfinate group or carboxylate group. From a synthetic chemical standpoint, L is any group which can function as a leaving group during nucleophilic substitution reactions. Representative examples of L are chloride, bromide, sulfonate. L can also be a divalent group such as sulfate or phosphate. Embodiments of L include chloro (Cl) or bromo (Br). Chloro (Cl) is particularly advantageous.

Haloalkyl silane reactants for use herein include 3-chloromethyl-1-triethoxysilane, 3-chloroethyl-1-triethoxysilane, 3-chloropropyl-1-triethoxysilane and 3-chlorobutyl-1-triethoxysilane. Of these, 3-chloropropyl-1-triethoxysilane is particularly advantageous.

The chemical equation(s) for reaction(s) between the aqueous thiocarboxylate salt(s) and the haloalkyl silane(s) to yield the thiocarboxylate silane(s) is(are) represented by Equations A, B, and C as follows:

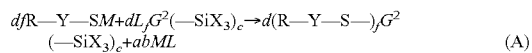

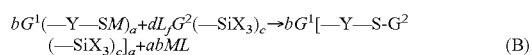

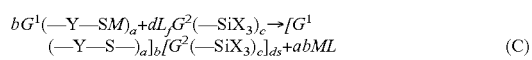

The preparation of the thiocarboxylate silane in accordance with the invention is carried out by combining and reacting haloalkyl silane and aqueous solution of thiocarboxylate salt in the presence of alkyguadinium salt catalyst, usually accompanied by agitation, e.g., stirring, until the reaction has reached the desired level of completeness. Additional salt(s) may optionally be present or be added to the aqueous thiocarboxylate salt to increase the ionic strength of the solution so as to further stabilize the product silane(s) against hydrolysis. Examples of such additional salts include alkali metal salts such as the sodium and potassium halides and the corresponding carbonates and nitrates. These and similar salts can be present in the reaction medium at a level of up to about 50, and advantageously up to about 20 weight percent of the amount of thiocarboxylate salt reactant present therein.

The level of completeness of the reaction can be monitored by any means which distinguishes the reactants from the products, such as, for example, gas chromatography (GC), liquid chromatography (LC or HPLC), nuclear magnetic resonance spectroscopy (NMR), or infrared spectroscopy (IR) of the organic phase, or wet chemical analysis of the aqueous phase.

Suitable reaction conditions include temperatures of from about −30° C. to about 300° C. and pressures of ambient to about 100 atmospheres or vacuum from ambient to about 0.01 torr. Specific embodiments include conditions of from about −10° C. to about 100° C. at ambient pressure. Additional embodiments include reaction temperatures of from about 25° C. to about 100° C., and advantageously from about 40° C. to about 95° C. Variable temperatures within the aforementioned ranges may be employed, as, for example, a gradual upward or downward ramping of the temperature during the course of the reaction.

Ordinarily, and by way of reducing the amount of siloxane-type by-product(s) that may be formed during the thiocarboxylate silane-forming reaction, it is advantageous to conduct this reaction under continuous agitation, e.g., that provided by the motion of a conventional rotary stirrer. The vigorousness of the agitation will ordinarily be such as to keep the amount of siloxane-type by-product(s) produced during the thiocarboxylate silane-forming reaction to within reasonable bounds, e.g., less than about 20 weight percent, more commonly less than about 12 weight percent, and typically to within about 5 to about 10 weight percent, of the total amount of reaction product. The amount of agitation required to achieve this can be determined in a specific case by routine experimentation.

Suitable concentrations of the starting aqueous thiocarboxylate salt are from about 1 weight percent up to saturation, which can be as high as about 50 weight percent or more. Particular concentrations include from about 20 to about 45 weight percent and from about 30 to about 40 weight percent. Optionally, an excess of the thiocarboxylate salt relative to that demanded by the reaction stoichiometry may be used to drive the reaction to completion so as to obtain a product of minimal residual haloalkyl silane starting material, to obtain the product with minimal reaction time and/or temperature, and/or to obtain a product with minimal loss to, or contamination by, silane hydrolysis/condensation products. Alternatively, an excess of the haloalkyl silane relative to that demanded by the reaction stoichiometry may be used to reduce the residual aqueous thiocarboxylate salt content at the completion of the reaction to a minimum.

The reaction may be run neat (i.e., without solvent) or in the presence of solvents which are insoluble or have limited solubility in water. Examples of appropriate solvents are ethers, for example, diethyl ether; hydrocarbons, for example, hexane, petroleum ether, toluene, and xylene; and ketones, for example, methyl ethyl ketone. Toluene or xylene are particularly advantageous. It is frequently advantageous to run the reaction neat.

Upon completion of the reaction, agitation is ceased resulting in the separation of the reaction mixture into two liquid phases. The organic phase (typically the upper phase) contains the thiocarboxylate silane product and the aqueous phase contains the coproduced salts plus any salts initially present or subsequently added to increase the ionic strength of the reaction medium. If a starting aqueous solution of sufficient concentration is used, a solid phase comprised of precipitated or crystallized salts may also separate. These salts may optionally be dissolved by addition of water so as to obtain a mixture made up of mainly or exclusively of two liquid phases. These phases can then be separated by decantation. Any solvents used during the process may then be removed by distillation or evaporation. Residual water may be removed by vacuum and/or heat stripping. Residual particulates may subsequently or concurrently be removed by filtration. Residual haloalkyl silane may be removed by stripping under vacuum at elevated temperature.

Preparation of Aqueous Thiocarboxylate Salt Reactant

If an aqueous solution of the thiocarboxylate salt(s) required for the preparation of the thiocarboxylate silane composition is not available, it may be prepared in a separate step preceding its use in the preparation of the thiocarboxylate silane composition. Alternatively, the aqueous thiocarboxylate salt may be prepared in situ and used directly thereafter, as described above, to prepare the thiocarboxylate silane composition.

If the thiocarboxylate salt is available, the aqueous solution thereof can simply be prepared by dissolving the appropriate amount of the salt into the appropriate amount of water to provide a solution of the desired concentration, or it can be prepared by dilution or evaporative concentration of whatever solution is available. Alternatively, the desired thiocarboxylate salt or aqueous solution thereof can be prepared from another salt of the desired thiocarboxylic acid. It the thiocarboxylic acid is available, the thiocarboxylate salt or aqueous solution thereof can be prepared simply by neutralizing the acid with a suitable base.

However, if neither the desired thiocarboxylic acid or one of its salts is available, it can be prepared by synthesis of the thiocarbonyl group by reaction of the appropriate acid halide and/or acid anhydride (e.g., the acid chloride) with an aqueous solution of a sulfide, a hydrosulfide, or mixture thereof (e.g., aqueous sodium hydrosulfide, NaSH), to yield an aqueous solution of the thiocarboxylate salt. If an aqueous mixture of thiocarboxylate salts is desired, the component thiocarboxylate salts can be blended, or the appropriate mixture of acid halides and/or acid anhydrides can be used in the preparation of the thiocarboxylate salts. Mixtures of one or more acid halides and acid anhydrides can optionally be used, as can mixtures of different sulfides and/or hydrosulfides when preparing either single-component or mixtures of aqueous thiocarboxylate salts.

Structures for the sulfides, hydrosulfides, and acid halides and acid anhydrides are represented by Formulae 6, 7, and 8, respectively.

$$M_2S \qquad (6)$$

$$MSH \qquad (7)$$

$$G^1(-Y-L)_a \qquad (8)$$

wherein each occurrence of M is an alkali metal; ammonium; or a mono-, di-, or tri-substituted ammonium; each occurrence of L is a halogen atom (i.e., F, Cl, Br, or I), sulfonate group, sulfinate group, or carboxylate group; Y is carbonyl, C(=O); each occurrence of R is chosen independently from the set of groups comprising hydrogen, alkyl groups that may or may not contain unsaturation, alkenyl groups, alkynyl groups, aryl groups and aralkyl groups with each R containing from 0 to 30 carbon atoms; each separate occurrence of $G^1$ and $G^2$ is independently R or a polyvalent group derived by substitution of an alkyl, alkenyl, aryl or aralkyl group, wherein $G^1$ and $G^2$ can contain from 1 to 40 carbon atoms, with the proviso that $G^1$ and $G^2$ are not hydrogen; each occurrence of X is independently a member selected from the group consisting of RO—, $R_2C$=NO—, $R_2NO$— or $R_2N$—, —R, and —$(OSiR_2)_c(OSiR_3)$, wherein each R is as above and at least one X is not —R; each occurrence of the subscript a is independently an integer from 1 to 6; each occurrence of the subscript b is independently an integer from 1 to 100; each occurrence of the subscript c is independently an integer from 1 to 6; each occurrence of the subscript d is independently an integer from 1 to 100; and each occurrence of the subscript f is independently an integer from 1 to 6, with the proviso that ab=df.

M is an alkali metal; ammonium; or a mono-, di-, or tri-substituted ammonium. Thus, M is typically a monocation, meaning it occurs as a cation, typically with a single positive charge. Dicationic ions could also be used in cases where their sulfides or hydrosulfides are available, suitably stable, and are sufficiently soluble in water. As such, M is the counterion to the anionic sulfide or hydrosulfide anion. Representative examples of M are sodium, potassium, ammonium, methyl ammonium, and triethyl ammonium. Sodium, potassium, and ammonium are especially advantageous.

L is a halogen atom (i.e., F, Cl, Br, or I), sulfonate group, sulfinate group, or carboxylate group. Representative examples of L are chloride, bromide, and any carboxylate, such as acetate, octanoate, decanoate, and dodecanoate. L could even be a divalent group, such as sulfate or phosphate. Specific embodiments include those where L is chloride (Cl) or carboxylate with Chloride (Cl) being particularly advantageous. In the case where L is chloride, the reagent is an acid chloride. Where L is carboxylate, the reagent is an acid anhydride. In the descriptions which follow, of the procedures for the preparation of aqueous thiocarboxylate salt solutions, it is to be understood, herein, that 1) The term acid halide shall refer to the acid fluoride, acid chloride, acid bromide, acid iodide, acid anhydride, or mixed acid anhydride with another carboxylic acid, other organic acid, or an inorganic acid; or any mixture thereof;
2) The term sulfide shall refer to an alkali metal, ammonium, or substituted ammonium sulfide salt; or any mixture thereof; and
3) The term, thiocarboxylate salt, shall refer to a single-component or mixture of salts of one or more than one thiocarboxylate and/or counterion (cation).

Chemical equations for reactions between the aqueous sulfides and/or hydrosulfides and the acid halides and/or acid anhydrides to yield the aqueous thiocarboxylate salts are illustrated by Equations D, E, F, and G.

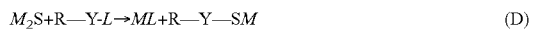

$$M_2S+R-Y-L \rightarrow ML+R-Y-SM \quad (D)$$

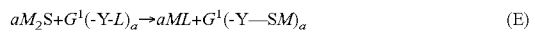

$$aM_2S+G^1(-Y-L)_a \rightarrow aML+G^1(-Y-SM)_a \quad (E)$$

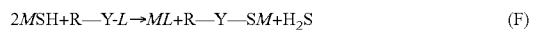

$$2MSH+R-Y-L \rightarrow ML+R-Y-SM+H_2S \quad (F)$$

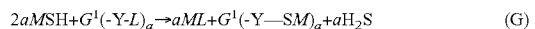

$$2aMSH+G^1(-Y-L)_a \rightarrow aML+G^1(-Y-SM)_a+aH_2S \quad (G)$$

The preparation of the aqueous thiocarboxylate salt is carried out by addition of the acid halide and/or acid anhydride to an aqueous solution of the sulfide and/or hydrosulfide and agitating the mixture. Due to the corrosive properties of the acid halide and/or acid anhydride, practical considerations suggest that this reaction be carried out in glass or in a glass-lined reactor.

An alkylguanidinium salt phase transfer catalyst may be added in one or several doses and/or in a continuous manner to the aqueous sulfide/hydrosulfide solution, the acid halide/acid anhydride, and/or the reaction mixture before, during, and/or after the addition of the acid halide/acid anhydride to the aqueous sulfide/hydrosulfide solution to accelerate the reaction.

Appropriate reaction conditions for the thiocarboxylate salt-forming reaction include temperatures of from about 10° C. to about 40° C., and advantageously from about 20° C. to about 25° C., for batch operation and from about 20° C. to about 50° C., and advantageously from about 25° C. to about 40° C., for continuous operation in order to minimize or suppress by-product formation.

Since the thiocarboxylate salt-forming reaction is fast and exothermic, in order the maintain the reaction within the aforesaid temperature conditions, it is advantageous to employ a reactor having temperature control capability, e.g., a jacket or coil through which a coolant such as chilled water or brine is circulated at an adjustable rate. In the absence of such temperature control capability, one can maintain the desired reaction temperature by controlling the rate of addition of the acid chloride reactant to the mixture of aqueous sulfide/hydrosulfide and phase transfer catalyst.

Additional conditions of the process for making the thiocarboxylate salt include a pressure of from about 0.01 torr to about 100 atmospheres, advantageously from about 100 torr to about 2 atmospheres, and a molar ratio of sulfide/hydrosulfide to acid chloride/acid anhydride of from about 2:1 to about 3:1, and advantageously from about 2:1 to about 2.2:1. The process is advantageously carried out with agitation of the reaction medium, e.g., employing a rotary stirrer, to minimize the formation of undesirable by-product(s). In general and when employing a rotary stirrer to provide agitation, the tip speed of the stirrer should be at least about 25 inches per second, advantageously at least about 30 inches per second with at least about 35 inches per second providing especially good results.

Concentrations of the starting aqueous sulfide/hydrosulfide can vary from about 1 weight percent up to saturation which can be as high as about 60 weight percent or more. Specific embodiments of concentrations include from about 10 to about 40 weight percent and from about 15 to about 25 weight percent. The reaction is usually complete when the acid halide/acid anhydride has dissolved in the aqueous phase, an exotherm is no longer evident from this reaction and the evolution of any hydrogen sulfide subsides. As previously stated, one or more additional salts may optionally be present or be added to the aqueous thiocarboxylate salt product to increase its ionic strength when used in the subsequent thiocarboxylate silane-forming reaction. At the completion of the thiocarboxylate salt-forming reaction, the solution may optionally be filtered to remove any particulate impurities and/or crystallized coproduced salts that may be present.

The Alkylguanidinium Phase Transfer Catalyst

The catalyst employed in the inventive process herein is a phase transfer alkylguanidinium salt. Useful alkylguanidinium salts, processes for their preparation and their uses as catalysts for other chemical syntheses are described in U.S. Pat. Nos. 5,081,298; 5,116,975; 5,132,423; 5,229,482; 5,830,974; 5,905,150; 5,907,025; 5,908,915; 6,028,203; 6,235,934; 6,570,038; and, 6,706,897, the entire contents of which are incorporated by reference herein. The phase transfer alkylguanidinium salt can be represented by Formula 9 as follows:

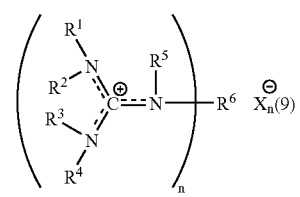

wherein each of $R^{1-5}$ is a primary alkyl radical and $R^6$ is a primary alkyl or bis(primary alkylene) radical, or at least one of the $R^{1-R2}$, $R^3-R^4$ and $R^5-R^6$ combinations with the connecting nitrogen atom forms a heterocyclic radical; X is an anion; and n is 1 or 2.

The alkyl radicals suitable as $R^{1-5}$ include primary alkyl radicals, generally containing about 1-12 and especially 1-6 carbon atoms. $R^6$ is usually an alkyl radical of the same structure or a C.sub.2-12 alkylene radical in which the terminal carbons are primary; in particular, R , is $C_{2-6}$ alkyl or $C_{4-8}$ straight chain alkylene. Alternatively, any combination of $R^{1-6}$ and the corresponding nitrogen atom(s) may form a heterocyclic radical such as piperidino, pyrrolo or morpholino radical.

X can be any anion, strong acid such as fluoride, chloride, bromide, iodide, sulfate, bisulfate and methanesulfonate, carbonate, bicarbonate, phosphate, carboxylate, thiocarboxylate and the like. Chloride and bromide ions are generally advantageous.

The value of n will be 1 or 2 depending on whether $R^6$ is alkyl or alkylene.

As indicated by the dotted bonds in the formula, the positive charge in the guanidinium salt is delocalized over one carbon and three nitrogen atoms. This is believed to contribute to the salts' stability under the relatively high temperature conditions encountered according to the invention. As a result, decomposition of the guanidinium salt does not occur or occurs only to a very minor extent under the conditions of the invention. The results include suppression of by-product formation and potential for continued use via recycle.

The alkylguanidinium phase transfer catalyst can be added to the reaction medium as salts, or as concentrated or dilute solutions in water and/or other suitable solvents, such as alcohols. The quantity of catalyst used will depend on the desired rate of reaction and the level of side products which can be tolerated, among other factors. Suitable concentrations include a concentration of from about 1 ppm (part per million by weight) to about 3 percent by weight. Specific embodiments of concentrations include from about 10 ppm to about 1 weight percent and advantageously from about 50 ppm to about 0.5 weight percent. Quantities below 1 ppm of phase transfer catalyst might be much the same as those obtained without the use of a phase transfer catalyst.

Specific examples of suitable alkylguanidinium phase transfer catalysts for use herein include those whose structures and chemical names appear below:

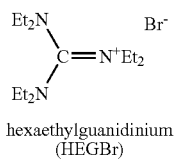
hexaethylguanidinium
(HEGBr)

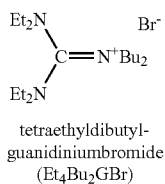
tetraethyldibutyl-
guanidiniumbromide
($Et_4Bu_2GBr$)

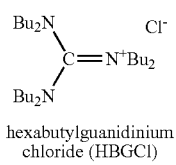
hexabutylguanidinium
chloride (HBGCl)

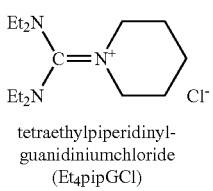
tetraethylpiperidinyl-
guanidiniumchloride
($Et_4pipGCl$)

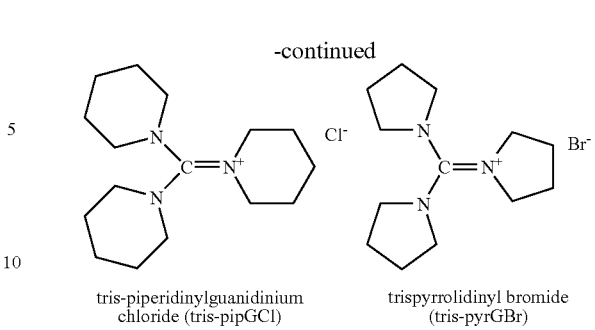
tris-piperidinylguanidinium
chloride (tris-pipGCl)

trispyrrolidinyl bromide
(tris-pyrGBr)

EXAMPLE 1

A. Preparation of Aqueous Sodium Thiooctanoate

A commercially available 337 grams of 45 weight % aqueous solution of sodium hydrogen sulfide (NaSH) was introduced into a 2 liter round bottomed flask with bottom take-off and 3 necks. The flask was provided with mechanical agitation, temperature control, addition funnel and reflux and take-off condenser. The material was diluted to 24% by adding 295 grams of water. To this agitated solution was added 1.7 grams of 34.5 weight % aqueous HEGCl solution at room temperature. 200 grams of octanoyl chloride were charged to the addition funnel and slowly added to the reaction mixture over 40 minutes while the flask was cooled with a water bath in order to maintain the temperature at 30-35° C. Very toxic hydrogen sulfide was released during the addition requiring special safety precautions to minimize exposure. The product was a clear aqueous solution of sodium thiooctanoate. The conversion was quantitative resulting in a purity of minimum 97 weight % sodium thiooctanoate based on the sodium octanoate by-product.

B. Preparation of 3-Octanoylthio-1-propyltriethoxysilane

The aqueous solution of sodium thiooctanoate was heated to 40° C. and 11 grams of 34.5% HEGCl solution were added. Also, about 296 grams of 3-chloro-1-propyltriethoxysilane were added batch-wise to the reaction mixture. The product was heated further to 90° C. and stirred for 5 hours. At this point, agitation was discontinued and the two-phase system was allowed to separate. The bottom aqueous phase was removed and the top crude product was recovered. The crude layer was purified by stripping the material at 135-145° C. and 5-10 mm Hg. The process yielded about 251 grams of pale yellow and clear product with a typical GC purity of 92-94%.

EXAMPLE 2-6

Examples 2-6 were carried in substantially the same manner as Example 1, the specific process conditions and results being set forth in the following table:

| Ex. | HEGCl, g | Temp. °C. | 60 min, wt % | 120 min, wt % | 180 min | Final purity by GC, wt % | Chloropropyltri-ethoxysilane, wt % | Total Heavies, wt % |
|---|---|---|---|---|---|---|---|---|
| 2 | 11 | 95 | 71.7 | 80.4 | 81.8 | 91.9 | 14.5 | 6.85 |
| 3 | 22 | 95 | 65.5 | 77.5 | 85.3 | 94 | 10.5 | 3.9 |
| 4 | 22 | 90 | 59.9 | 72.3 | 79.2 | 91.4 | 17.4 | 6.5 |
| 5 | 22 | 100 | 76.8 | 86.8 | | 75.4 | 8.2 | 23.3 |
| 6 | 0 | 95 | 64.2 | 73.1 | 78.4 | 87.3 | 17.9 | 9.4 |

The reactions in Examples 1-6 were monitored every hour by GC. The residual chloropropyltriethoxysilane in the crude was analyzed by GC. The final purity of the stripped material and the amount of heavies generated in the process are also given in the table.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

What is claimed is:

1. A process for the preparation of thiocarboxylate silane represented by the formula:

 (2)

which comprises reacting an aqueous solution of salt of thiocarboxylic acid represented by the formula:

 (4)

with a haloalkyl silane represented by the formula:

 (5)

with continuous agitation, at a temperature of between 40° C. and 95° C. and in the presence of a catalytically effective amount ranging from 1 part per million to 3 weight percent of alkylguanidinium salt phase transfer catalyst represented by the formula:

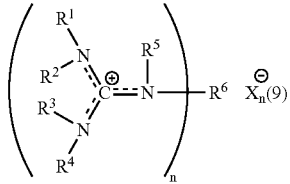

to provide thiocarboxylate silane containing less than 12 weight percent of siloxane-type by-product(s), wherein $G^1$ is R wherein R is chosen independently from the set of groups comprising hydrogen, alkyl groups that may or may not contain unsaturation, alkenyl groups, alkynyl groups, aryl groups, and aralkyl groups, with each R containing from 0 to 30 carbon atoms; $G^2$ is chosen from the group consisting of —$CH_2$—, —$CH_2CH_2$—, —$CH_2CH_2CH_2$— and —$CH_2CH(CH_3)$ $CH_2$—; Y is carbonyl, C(=O): each occurrence of X is independently a member selected from the group consisting of RO—, and —R, with the proviso that at least one X is not —R; L is a halogen; each $R^1$, $R^2$, $R^3$, $R^4$, $R^5$ and $R^6$ is a primary alkyl radical containing 1 to 6 carbon atoms; $X^-$ is chosen from the group consisting of chloride and bromide; $M^+$ is an alkali metal cation; the subscript a is 1; the subscript c is 1; the subscript f is 1; and the subscript n is 1.

2. The process of claim 1 wherein $M^{30}$ is selected from the group consisting of sodium cation and potassium cation.

3. The process of claim 2 wherein L is selected from the group consisting of chloride and bromide.

4. The process of claim 1 wherein the salt of thiocarboxylic acid is present in aqueous solution up to its maximum solubility therein under the reaction conditions.

5. The process of claim 1 wherein additional salt is present during the reaction to increase the ionic strength of the reaction medium thereby increasing the stability of the product thiocarboxylate silane from hydrolysis.

6. The process of claim 5 wherein the additional salt is selected from the group consisting of alkali metal halide, alkali metal carbonate and alkali metal nitrate.

7. The process of claim 5 wherein the concentration of the salt of thiocarboxylic acid in the aqueous solution thereof is from about 20 to about 45 weight percent.

8. The process of claim 1 wherein a stoichiometric excess of salt of thiocarboxylic acid or a stoichiometric excess of haloalkyl silane is present.

9. The process of claim 1 wherein the reaction is carried out in the substantial absence of organic solvent which is insoluble in water or has limited solubility in water under the reaction conditions.

10. The process of claim 1 wherein the reaction is carried out in the presence of organic solvent which is insoluble in water or has limited solubility in water under the reaction conditions.

11. The process of claim 1 wherein the alkylguanidinium salt is at least one member selected from the group consisting of hexaethylguanidinium bromide, tetramethyldibutylguanidinium bromide, hexabutylguanidinium chloride, and mixtures thereof.

12. The process of claim 1 wherein the catalyst is present in the reaction medium at a concentration of from about 10 parts per million to about 1 percent by weight.

13. The process of claim 1 wherein the product thiocarboxylate silane is selected from the group consisting of 2-triethoxysilyl-1-ethyl thioacetate; 2-trimethoxysilyl-1-ethyl thioacetate; 2-(methyldimethoxysilyl)-1-ethyl thioacetate; 3-trimethoxysilyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxysilyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 3-trimethoxysilyl-1-propyl thiooctanoate, also known as 3-trimethoxysilyl-1-propyl thioloctoate and 3-trimethoxysilyl-1-propyl thiocaprylate; 3-triethoxysilyl-1-propyl thiopalmitate; 3-triethoxysilyl-1-propyl thiooctanoate, 3-triethoxysilyl-1-propyl thiodecanoate; 3-triethoxysilyl-1-propyl thiododecanoate, 3-triethoxysilyl-1-propyl thiotetradecanoate, 3-triethoxysilyl-1-propyl thiobenzoate; 3-triethoxysilyl-1-propyl thio-2-ethylhexanoate and 3-triethoxysilyl-1-propyl thio-2-methylheptanoate.

14. The process of claim 1 wherein the haloalkyl silane is selected from the group consisting of chloromethyltriethoxysilane, 3-chloroethyl-1-triethoxysilane, 3-chloropropyl-1-triethoxysilane and 3-chlorobutyl-1-triethoxysilane.

* * * * *